May 9, 1950 W. B. CLARKE Plant Pat. 940
FLOWERING QUINCE PLANT
Filed June 13, 1949
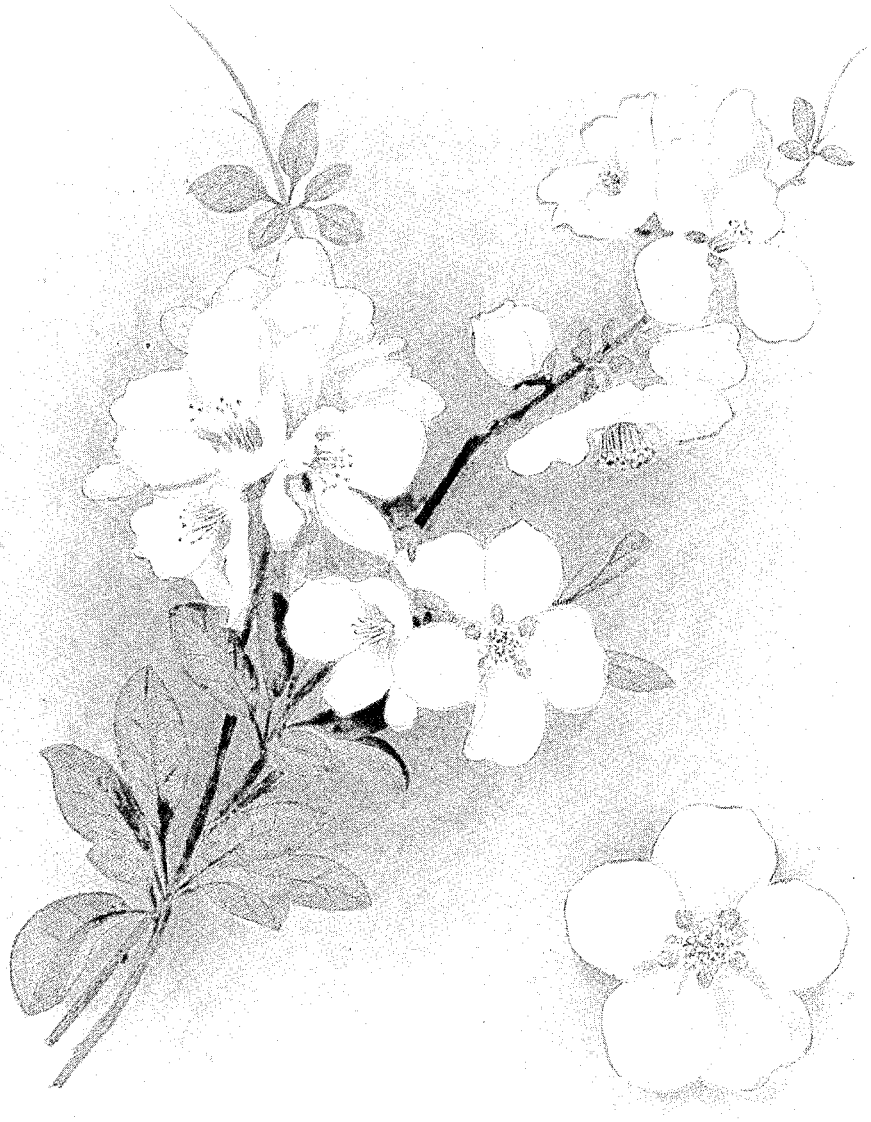
WITNESS
Addison F. Avery
INVENTOR
WALTER BOSWORTH CLARKE,
by Kummler Kummler & Snow,
ATTYS.

Patented May 9, 1950

Plant Pat. 940

UNITED STATES PATENT OFFICE

940

FLOWERING QUINCE PLANT

Walter Bosworth Clarke, San Jose, Calif., assignor to W. B. Clarke & Co., San Jose, Calif., a partnership Application June 13, 1949, Serial No. 98,763

1 Claim. (Cl. 47—60)

The present discovery is a new and distinct variety of flowering quince plant. It originated as a seedling discovered January 15, 1942, and belongs to the group *Chaenomeles superba*. The seed parent was C. *candida* crossed by an unknown variety and is the result of definite breeding efforts carried on by me since January 15, 1931. This new variety has been reproduced at Santa Clara County, California, by grafting through several generations and the resulting plants have conformed exactly to the original.

The novelty of this new variety resides primarily in the unique pink coloring of its large flowers, long blooming period and the profuseness of its bloom.

The accompanying painting shows in full color a spray of characteristic blooms and foliage, with a face view of a flower in a separate view.

Referring to the novel characteristics of this new variety, the flower is rather large, often attaining two inches in width. Its most unusual characteristic is the coloring of the blooms, which ranges from a pronounced azalea pink at the tip shading through an intermediate shrimp red tone to become almost white at the center. It has a very long blooming period. During the seven years it has been under test, it has bloomed continuously for a period of two months. It has bloomed twice at least in early and midseason and sometimes has a third crop later on.

The color designations of the flower colors are identified according to the British Horticultural Color Standards, and the foliage according to Maerz and Paul Dictionary of Color, in tabular form as follows:

| | |
|---|---|
| Darkest flower tone | Azalea pink, B. H. C. C. 618 |
| Lighter general tone | Shrimp Red, B. H. C. C. 616/3 |
| Center tone | Almost White |
| Main leaf green, Maerz & Paul | Plate 21, L, 6 |
| Under side of leaf, Maerz & Paul | Plate 21, J, 5 |
| Stem, Maerz & Paul | Plate 56, H, 2 |

In other respects and general plant structure, this new variety is similar to other flowering quince plants. It has terminal flowers consisting of the usual five petals, numerous stamens, and styles.

The following is a detailed description:

Parentage: Seedling.

*Seed parent.*—*Chaenomeles lagenaria* candida.

*Pollen.*—Unknown.

Classification: *Chaenomeles superba* (Rehder) var.

Plant:

*Form.*—Bush.

*Height.*—Probably about 5 feet maximum.

*Growth.*—Moderately vigorous and hardy.

*Foliage.*—Normal quantity. Petioles—length, ¼ to ½ in. Color—new foliage, soft green; old foliage, deep green. Size of leaf—small. Texture—leathery and glossy. Shape—ovate-lanceolate.

Thorns: Some.

*Color.*—Brown.

*Size.*—Same length as petioles.

Flower: Blooms profusely early and in midseason and sometimes has third crop later.

*Size.*—Large, 2 inches in width.

*Petalage.*—5.

*Form.*—Almost round, bluntly pointed and tending to have slightly ruffled tips.

*Color.*—Shrimp red with very light center.

*Texture.*—Usual with satiny appearance. It is apparently completely resistant to disease. As cut flowers open freely, if cut considerably before normal blooming time.

Bud:

*Size.*—Usual.

*Form.*—Bluntly pointed. Globular.

One of its pronounced and most distinctive characteristics is the shade variation in color from dark pink tip to white center of each flower petal. This combined with the size of the blossom and profuseness of bloom, and the very long blooming period enhances the value of this bush as a commercial product.

Having thus described my invention, I claim:

A new and distinct variety of flowering quince plant, substantially as described and illustrated, characterized particularly by the unusual color of the flowers, shading from dark pink tips to white centers, their large size, floriferousness, and the continuously long blooming period.

WALTER BOSWORTH CLARKE.

No references cited.